United States Patent [19]

Tellman et al.

[11] Patent Number: 5,973,223
[45] Date of Patent: Oct. 26, 1999

[54] IMPLANT FOR FIXING FEMORAL FRACTURES

[75] Inventors: Lars G Tellman, Falsterbo; Per J. A. Lagerman, Stockholm; Henrik Hansson, Linköping, all of Sweden

[73] Assignee: Collux AB, Malmo, Sweden

[21] Appl. No.: 09/040,130

[22] Filed: Mar. 17, 1998

Related U.S. Application Data

[63] Continuation of application No. 08/835,546, Apr. 8, 1997, Pat. No. 5,728,099, which is a continuation of application No. 08/332,890, Nov. 1, 1994, abandoned.

[30] Foreign Application Priority Data

Feb. 21, 1994 [SE] Sweden .................................. 9400609
Mar. 29, 1994 [SE] Sweden .................................. 9401057

[51] Int. Cl.[6] .............................. A61F 2/28; A61B 17/58
[52] U.S. Cl. ................................ 623/16; 606/65; 606/67; 606/69; 606/71
[58] Field of Search .................................. 606/65, 67, 69, 606/71, 68, 60; 623/16, 18, 22, 23

[56] References Cited

U.S. PATENT DOCUMENTS

| | | | |
|---|---|---|---|
| 2,526,959 | 10/1950 | Lorenzo | 128/92 |
| 2,612,159 | 9/1952 | Collison | 128/92 |
| 2,702,543 | 2/1955 | Pugh et al. | 128/92 |
| 2,801,631 | 8/1957 | Charnley | 128/92 |
| 3,374,786 | 3/1968 | Callender, Jr. | 128/92 |
| 3,400,711 | 9/1968 | Hux et al. | 128/92 |
| 3,547,114 | 12/1970 | Haboush | 128/92 |
| 3,782,374 | 1/1974 | Fischer | 128/92 BB |
| 3,900,025 | 8/1975 | Barnes, Jr. | 128/92 D |
| 3,987,499 | 10/1976 | Scharbach et al. | 3/1.91 |
| 3,996,931 | 12/1976 | Callender, Jr. | 128/92 BA |
| 4,095,591 | 6/1978 | Graham, Jr. et al. | 128/92 BB |
| 4,379,451 | 4/1983 | Getscher | 128/92 CA |
| 4,438,762 | 3/1984 | Kyle | 128/92 BB |
| 4,441,492 | 4/1984 | Rydell et al. | 128/92 EB |
| 4,628,923 | 12/1986 | Medoff | 128/92 YV |
| 4,776,330 | 10/1988 | Chapman et al. | 128/92 YY |
| 4,795,473 | 1/1989 | Grimes | 623/23 |
| 4,973,332 | 11/1990 | Kummer | 606/65 |
| 5,041,114 | 8/1991 | Chapman et al. | 606/62 |
| 5,190,544 | 3/1993 | Chapman et al. | 606/69 |
| 5,484,439 | 1/1996 | Olson et al. | 606/65 |

FOREIGN PATENT DOCUMENTS

| | | |
|---|---|---|
| 2149943 | 3/1973 | France . |
| 918531 | 9/1954 | Germany . |
| 1812973 | 4/1993 | Russian Federation . |

OTHER PUBLICATIONS

FR 2,149,943 is represented by its US equivalent cited above US 3,782,374.
Derwent Abstract of RU 1812973 (Abstract Only).
Massie, W. "Massie Sliding Nail." Warsaw, In., 1981, Catalog, p. B170.

Primary Examiner—David H. Willse
Assistant Examiner—Dinh X. Nguyen
Attorney, Agent, or Firm—Ladas & Parry

[57] ABSTRACT

The present implant is for fixing femoral fractures and the like. The implant consists of three main parts, namely a first part consisting of an angle element, a second part which forms a holder and a third part in the form of a screw. The angle element includes a sleeve for receiving the screw. Both the sleeve and the screw are intended to be passed into a channel provided through the neck and head of the femur of a patient. The angle element moreover includes a slide which is slidingly accommodated by the holder. The holder is, in its turn, secured by means of anchorage screws in the shaft of the femur. By cooperation between the slide and the holder the possibility is afforded that the angle element may move in relation to the shaft of the femur. The sleeve of the angle element is disposed at an angle in relation to the slide.

22 Claims, 6 Drawing Sheets

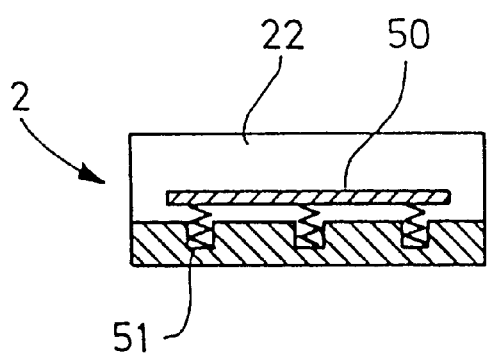
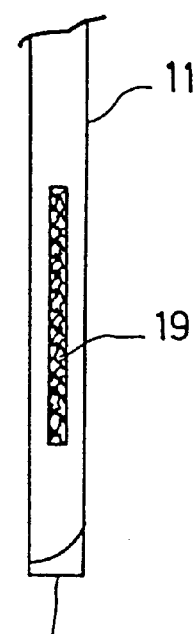
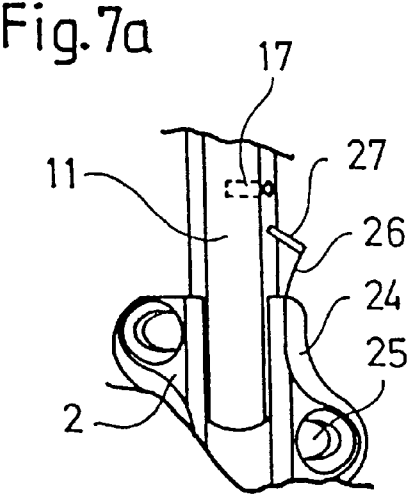
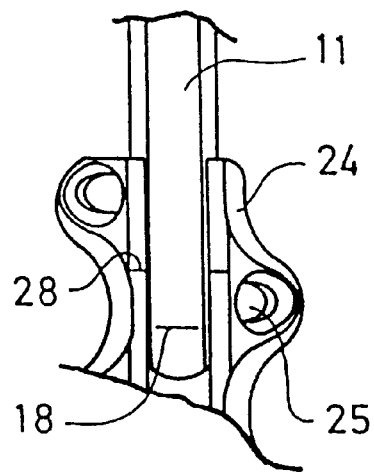
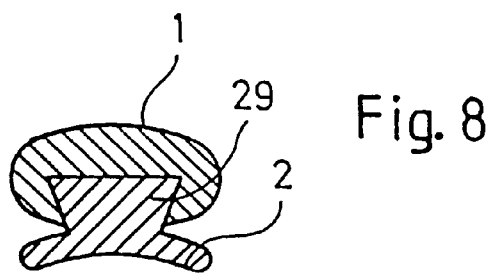

IMPLANT FOR FIXING FEMORAL FRACTURES

"This is a continuation of application Ser. No. 08/835,546 filed on Apr. 8, 1997 (now U.S. Pat. 5,728,099 issued Mar. 17, 1998) which is a continuation of Ser. No. 08/332,890 filed Nov. 1, 1994 (now abandoned), claims the benefit thereof and incorporates the same by reference."

FIELD OF THE INVENTION

The present invention relates to implants for fixing femoral fractures

BACKGROUND

The term femoral fractures is here taken to signify intertrochanterian, subtrochanterian and supracondylar fractures, i.e. fractures at different places of the thigh bone (femur).

In order to promote the healing of femoral fractures, use has been made for a relatively long time of various types of screws or pins for fixing the loose bone pieces in such mutual positions that the growing together of the bone pieces across the sides of the fracture is promoted.

In intertrochanterian fractures or fractures which are both inter-trochanterian and subtrochanterian, the orthopedist has, to support the bone pieces around the fracture, often chosen in accordance with techniques hitherto employed to use a fixation device (implant) comprising a screw and an angled plate with which the screw is connected. The screw is passed, via a bore, into the head of the femur and is thereafter screwed in place therein. The plate is secured to the femur by means of screws of considerably smaller dimensions than the previously mentioned screw. The head of the femur and the femur proper have thereby obtained mutually fixed positions even if the fixation device permits a certain, very limited possibility for sliding in the longitudinal direction of the neck of the femur. On the other hand, the plate secured to the femur has always been arranged to realize a completely rigid fixation of the plate in the longitudinal direction of the femur.

While operations in which such fixation devices are applied normally give the desired outcome, it is not uncommon that problems occur because of excessive loading on the fixation device. Excessively high loading entails, for example, that the plates or their anchorage screws break off, that the smaller anchorage screws are projected out of their holes in the bone some time after the operation or that the large screw up through the neck of the femur cuts through the surface definition of the head of the femur towards the hip joint. Such problems are naturally extremely negative, involve pain to the patient and often entail that a new operation must be carried out.

Moreover, the technique disclosed in the immediately preceding paragraphs entails the disadvantage that the fracture surfaces after being subjected to loading, are occasionally fixed in positions in which the surfaces do not fit into one another, a factor which both prolongs and impedes the healing process. This results in bone shortening, lameness and difficulties in walking.

SUMMARY OF THE INVENTION

The implant according to the present invention eliminates the above-indicated disadvantages inherent in prior art employed implants and makes it possible better to utilize the natural healing processes of the human body. The implant also entails that the body, when necessary, corrects the mutual positions of the fracture pieces so that the fracture pieces, once the operation has been completed and the patient subjects the area to load by walking, assume more optimum positions favorable for the process of healing and growing together. This is effected in that the implant is of a construction which permits both contraction and separation movements in the axial direction of the shaft of the femur and in the direction of the hole made in the head of the femur. In addition, the implant according to the present invention permits movements transversely of the longitudinal direction of the shaft of the femur to a degree which corresponds to a maximum displacement of the fracture surfaces in relation to one another of up to between 5 and 7 mm.

It is not only those forces which occur in normal loading to which the implant is subjected. When the patient is anaesthetized during the operation, the muscles are wholly relaxed, but when the patient recovers from the anaesthetic after the operation, considerable muscular contractions take place. This causes considerable compression forces on the fracture. In such an event, these forces are directed substantially along the axial direction of the shaft of the femur. The implant according to the present invention is of such construction that those movements caused by the muscular contraction are absorbed and controlled by the implant.

As was mentioned above, it is important that the implant permits movement along the shaft of the femur. The only type of angled implant for fractures of the femur of which we are aware and which permits the sliding movement disclosed by way of introduction is disclosed in U.S. Pat. No. 4,628,923. However, the sliding movement is restricted by the use of a distal screw. No movement transversely of the direction of the shaft of the femur is either mentioned or intimated in the patent specification. The above-described sought-for function in the implant is achieved according to the present invention by providing relative movement of respective slidable portions of a holder anchored to the femur and of a slide carrying an anchorage screw also anchored to the femur. The holder and slide are not directly connected to one another so that their sliding portions can move relative to one another and accommodate changes in the femur during loading thereof.

Applying the solution according to the present invention, there will be obtained an implant which is flexible in that it can be employed in many different fracture formations, and in which the natural healing powers of the human body are supported instead of, as is sometimes the case in the employment of prior art implants, impeding and obstructing the natural healing conditions.

In order to create as small an operation incision as possible, the portion fixed to the shaft of the femur must have as slight axial extent as possible in the longitudinal direction of the shaft of the femur.

The implant according to U.S. Pat. No. 4,628,923 suffers from the drawback that the operational incision will be relatively long, since the implant is of a construction which requires that the operation incision be made longer than the retainer element itself. The reason for this long operational incision is that there must be room to allow for operating a compression screw or so-called distal screw disposed in the axial direction of the retainer element, which lengthens the operational incision by approx. 5 cm or more. Yet a further disadvantage is that the locking of the rotational movement between the cooperating parts of the implant is complicated, in that the circular cross-section necessitates a solution in which rotational movements are prevented, this being attained in the patent by means of a tongue and groove.

In one embodiment of the implant according to the present invention, the implant has a construction which entails that, when it is to bridge over a certain length of the shaft of the femur, the advantage will be attained that the requisite length of the implant is less than the length which is required in the implant according to U.S. Pat. No. 4,628,923. This is achieved in that the sliding portion of the second part is disposed to permit the lower end of the sliding portion to pass the lower end of the sliding portion of the second part.

There is a series of, to some extent contrary, demands placed on an implant for fixing femoral fractures. The basic requirement is that the implant must be sufficiently powerful in order to be able to absorb those forces to which it is expected to be subjected, without risking breakage. For the orthopedist, it is important that the implant is simple to handle so that he/she can quite simply concentrate on applying it in place. In an alternative embodiment of the present invention the implant is, therefore, arranged so as to permit the mutually sliding parts, to be temporarily and adjustably fixed to one another until the implant is in place.

There are further requirements that the implant should follow and connect as closely as possible to the bone and project out as little as possible from the femur, in order that the patient does not suffer from greater discomfort than is absolutely necessary.

In order, if possible, to avoid the risk that the orthopedist places the different implant parts too far apart, which could result in such large torque forces being applied that there is a risk of breakage, the implant is, in one embodiment, provided with a mechanical stop which prevents sliding movement past a certain critical position. In one alternative embodiment, the point which may not be passed on a sliding movement is shown by markings.

Yet a further advantageous feature of the implant according to the present invention is that the retainer plate is designed so that the screws which are secured in the femur will be in place crosswise, which improves stability.

BRIEF DESCRIPTION OF THE DRAWINGS

The present invention will now be described in greater detail hereinbelow, with the aid of embodiments shown on the drawings. In the accompanying drawings:

FIG. 3 is a cross-sectional view taken along the line III—III in FIG. 1 or FIG. 1a;

FIG. 4 is an end elevation of one of the details in the embodiments of FIG. 1 or FIG. 1a;

FIGS. 5a,b, 6a,b show different methods of arranging temporary locking of the sliding movement between the different parts included in the embodiments according to FIG. 1 or FIG. 1a;

FIG. 7a is a detailed view of a locking device;

FIG. 7b is a detailed view of the placing of markings;

FIG. 8 is a cross-section corresponding to that of FIG. 3 of an alternative embodiment;

DETAILED DESCRIPTION OF PREFERRED EMBODIMENTS

Figure 1:
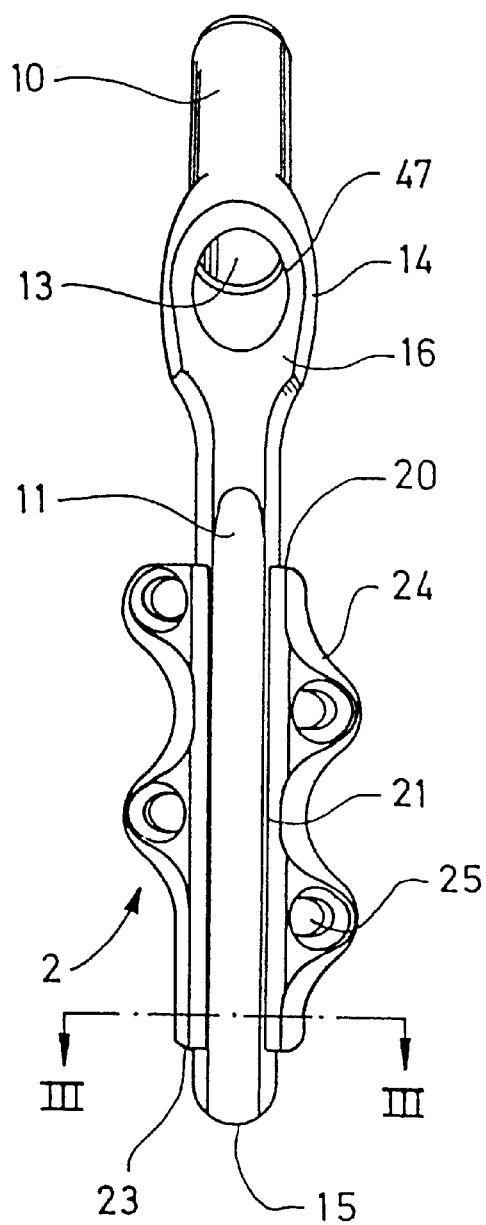
FIG. 1 is a top plan view of one embodiment of the implant.

In the embodiment shown in the FIGS. (cf. FIGS. 1 and 2), the implant consists of three main parts, namely a first part constituting an angle element 1, a second part forming a holder 2 and a third part in the form of an anchorage device 3 and shown in the FIG.s in one preferred embodiment in which it is in the form of a screw (lag screw) 3, hereinafter designated main screw 3.

The angle element 1 has a first section which substantially consists of a sleeve 10, and a second section which substantially consists of a slide 11. In the region 14 where the sleeve 10 merges into the slide 11, the angle element 1 displays a portion 16 which is thickened in relation to the slide 11. The thickened portion forms the upper region of the slide. The central cavity 13 of the sleeve 10 is arranged to receive the main screw 3 preferably with tight fit. One opening 47 of the central cavity is located in the thickened portion 16. The slide 11 is intended to be disposed substantially parallel with the shaft of the femur. The section between the transitional region 14 and the lower end 15 of the slide forms the sliding portion 11 of the first part 1.

Figure 2:
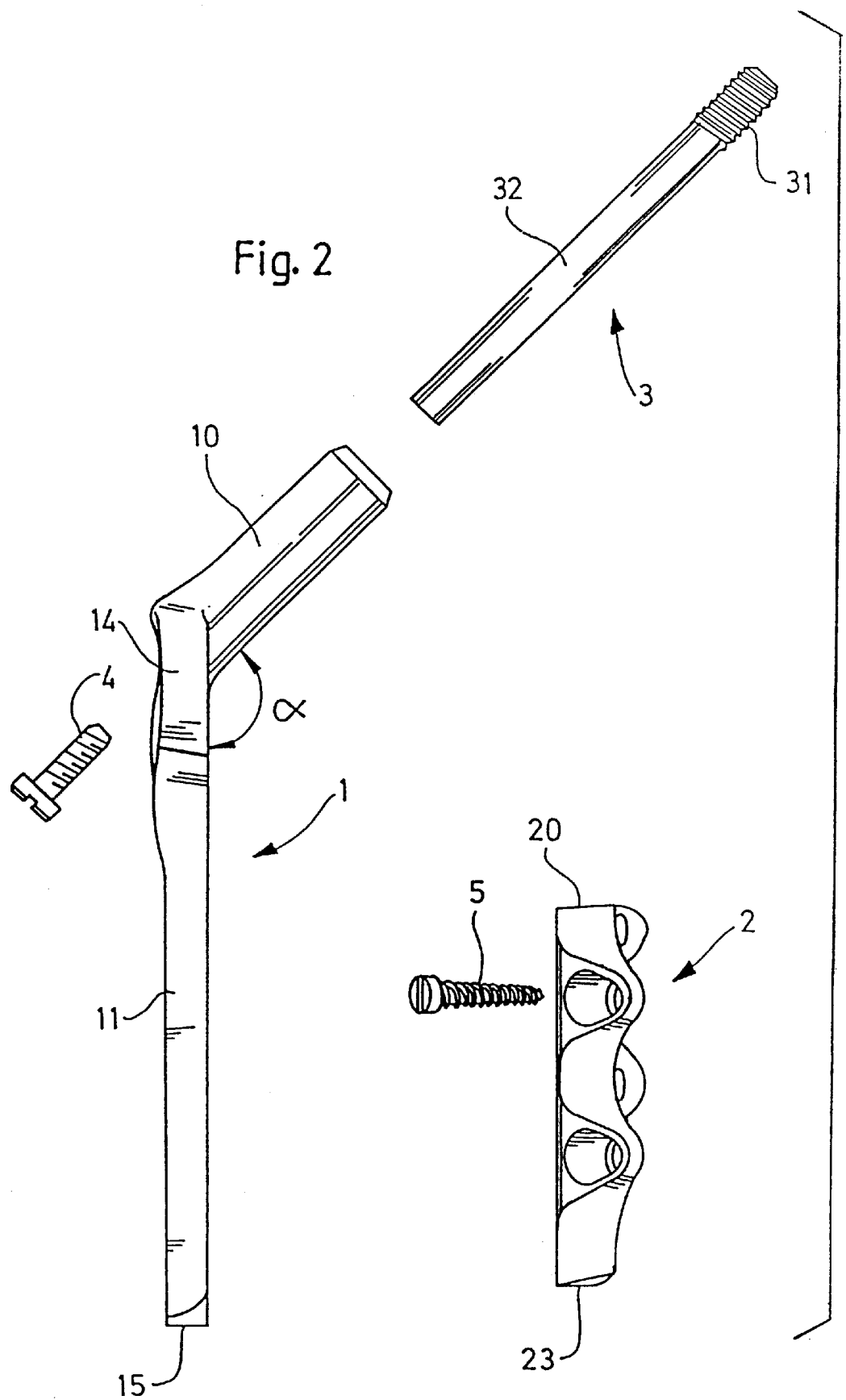
FIG. 2 is an exploded view of the apparatus of FIG. 1 seen from the side.

The sleeve 10 is disposed at an angle α in relation to the slide (cf. FIG. 2). Normally, the angle cc is of the order of magnitude of between 120–150°. Preferably said angle α varies between 130° and 140°, and, as a rule is approx. 135°. In other embodiments intended for special types of fractures and bone sizes, the angle α varies further.

Figure 3:
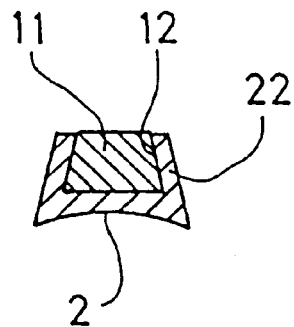

As is apparent from FIG. 3, the slide 11 has, in the illustrated embodiment, sloping side walls 12 where the width of the slide 11 surgically inserted with the implant decreases in a direction away from the femur.

Figure 1A:
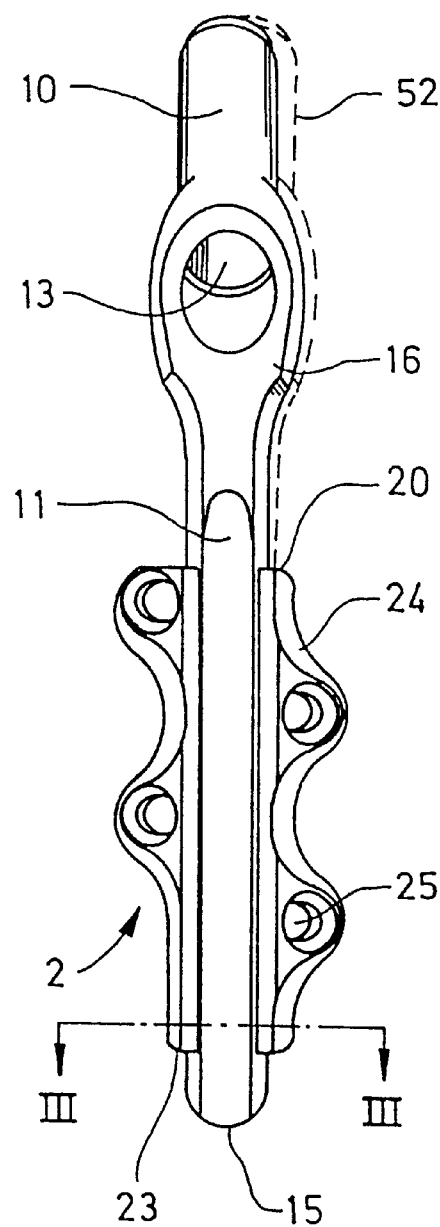
FIG. 1a is a top plan view illustrating the movability of the implant.
Figure 4:
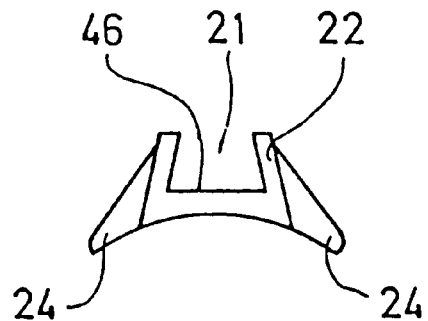
Figure 9:
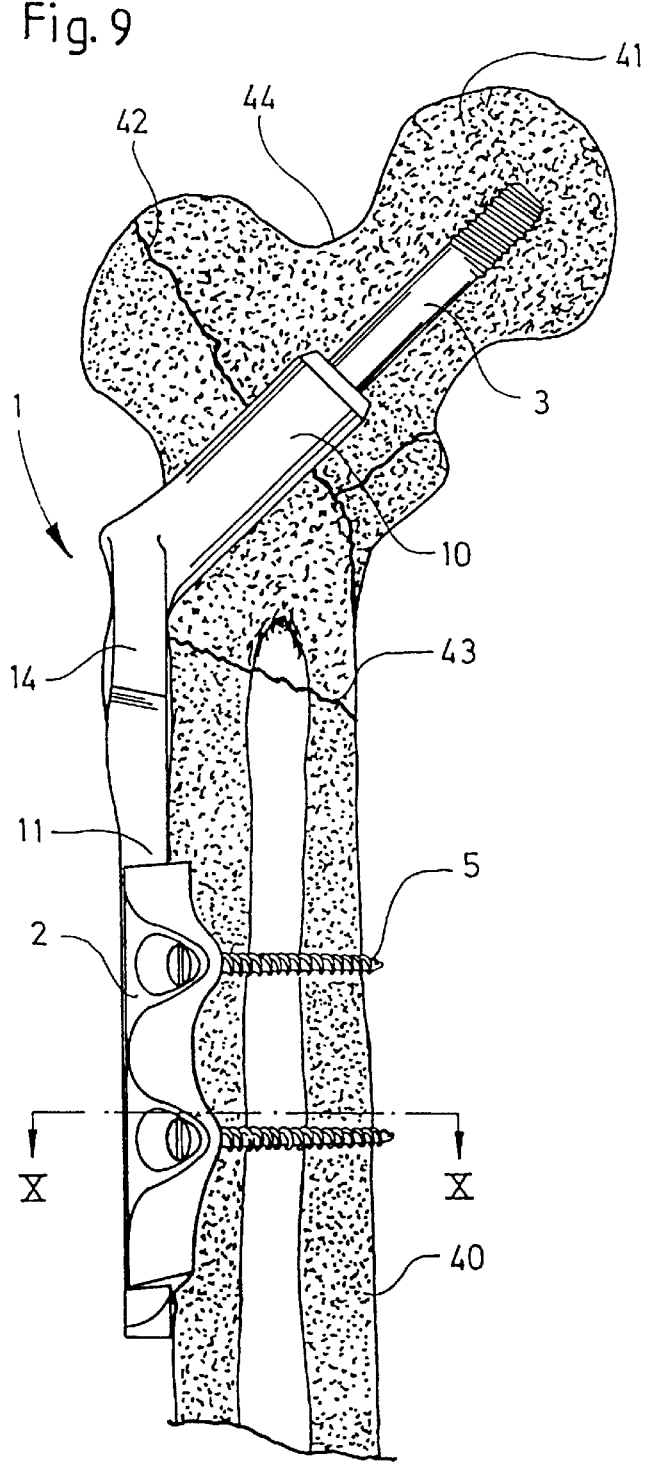
FIG. 9 shows an implant according to the present invention fixed to the femur.

In the embodiment illustrated in FIGS. 1,1a and 9, the holder 2 displays a groove 21 (cf. FIG. 4) of a cross-sectional configuration which corresponds to the cross-sectional configuration of the slide 11, i.e. the groove displays side walls 22 which slope towards one another. The groove 21 forms the sliding portion 21 of the second part 2. The holder 2 moreover has a number of flange portions 24 through which holes 25 are provided for receiving screws 5 which are intended to be secured in the femur. These screws are of smaller dimensions than the main screw 3 and are hereinafter generally referred to as anchorage screws 5. The groove 21 on the holder 2 is throughgoing, i.e. it has no stop abutment at the ends of 20,23 the groove whereby the entire groove length in this embodiment can be utilized for accommodating the slide 11, which entails that the operational incision will be kept short. The absence of stop abutments entails that one and the same holder 2 can be employed for angle elements 1 with different lengths of the slide 11.

Figure 10:
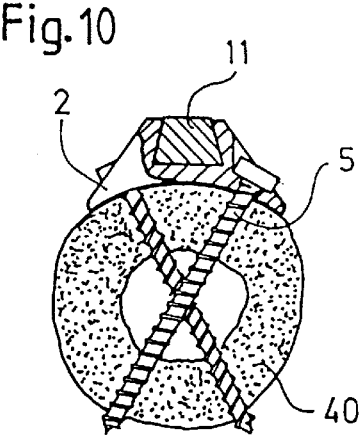
FIG. 10 is a cross-section taken along the line X—X in FIG. 9.
Figure 11:
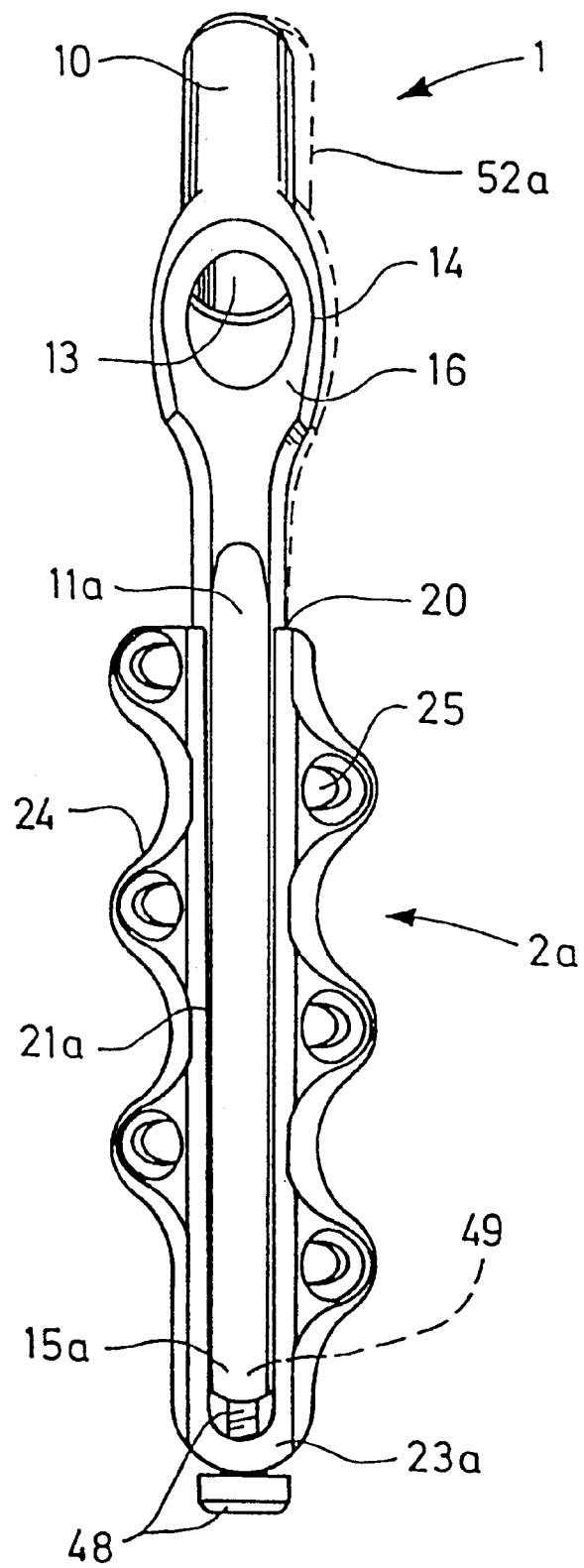
FIG. 11 is a top plan view of an alternative embodiment of the implant.

The holder 2a according to the embodiment in FIG. 11 differs from the holder 2 according to the above-described embodiment only in that the groove 21a is closed at the lower end 23a. A distal screw 48 passes through a bore in the lower end 23a of the holder and is received in a threaded bore 49 in the lower end 15a of the slide 11a. The head of the distal screw abuts against the lower edge of the holder, whereby the slide 11a is displaced upwardly or downwardly in the groove 21a of the holder 23a when the screw is rotated, and therewith the sleeve 10 of the angle element 1. Other reference numerals have their counterparts in those previously defined in the description of FIGS. 1–10. This type of holder is employed, for example, if there is a need for an implant which makes it possible to apply a compression force in the axial direction of the shaft of the femur.

The axial length of the holder 2 is, in the embodiment illustrated in FIGS. 1,1a,9 and 10, shorter than the axial length of the sliding portion 11 of the first part, whereby the operational incision can be kept short. A further feature of the illustrated embodiment which makes possible short operational incisions is that the hole 25 for the lower-most anchorage screw 5 is disposed a distance from the lower edge 23 of the holder 2. The operational incision need not be longer than it provides access for screwing in the lowermost anchorage screw 5. Those parts of the implant which are located lower down can be moved into place without needing to make an incision for the region below the lowermost anchorage screw 5. This is effected in that the tissue is temporarily lifted up below the region of the lowermost screw, whereafter the implant is passed in beneath the raised tissue.

Even though the holders 2,2a are provided, in the illustrated embodiments, with holes 25 for four or six anchorage screws 5, the present invention is not restricted to implants exclusively including holders having this number of holes. If necessary, a larger number of holes, for example 8 or 10, and so on, may be employed.

In the illustrated example, the anchorage means consist of the main screw 3 with a thread 31 and a shaft 32 which fit into the sleeve 10. The screw 3 is disposed, if desired, to be lockable in relation to the sleeve 10 with the aid of a clamping screw 4 which is screwed into a threaded opening (not shown) in the end of the screw shaft 32. The illustrated screw 3 should only be seen as an example of one embodiment, and given that the invention is not dependent upon the exact design of the screw 3, this will not be described in greater detail. It is obvious that the anchorage device may be of varying designs, for example a nail, a pin, a bolt provided with projecting anchorage means in its end, etc.

FIG. 9 shows one example of how an implant according to the invention is fixed at the femur in a femoral fracture comprising both an intertrochanterian fracture 42 and a subtrochanterian fracture 43. As is apparent from the FIG., the main screw 3 is secured in a channel through the neck of the femur 44 and the head of the femur 41, and the holder 2 is fixed with the aid of anchorage screws 5 in the shaft 40 of the femur.

FIG. 1a illustrates one embodiment of the invention in which the crosssection of the sliding portion 21 of the holder 2 and the sliding portion 11 of the angle element 1 are dimensioned such that there exists a certain clearance between both of the sliding portions. The conical cross sections entail that this clearance is at its greatest when the slide 11 is most proximal the bottom 46 of the groove 21. The dimensional differences of the cross-sections are selected such that the maximum permitted displacement of the opening 47 from a neutral position i.e. when the sliding portions 11 and 21 are aligned and centered, is less than approx. 7 mm and as a rule approx. 5 mm. The clearance which is required for sliding to occur is normally approx. 0.02 mm.

By cooperation between the sliding portion 11 of the slide and the sliding portion 21 of the holder 2, it is possible that the angle element 1 can move axially along the shaft of the femur 40. In the embodiment illustrated in FIG. 1a, a certain limited movement is also made possible in a plane substantially at right angles to the axial direction of the slide. The parts are manufactured from a material which gives low friction between the different sliding portions of the parts, for example surface-treated stainless steel.

The movement transversely of the shaft of the femur 40 is illustrated in FIGS. 1a and 11 by broken lines 52,52a. It will be obvious to a person skilled in the art that the broken lines 52,52a merely indicate one of the possible directions of movement transversely of the axial direction of the slide. In those embodiments in which the construction of the implant permits movements transversely of the axial direction of the slide, such movement takes place in that direction occasioned by the relevant loading of the implant.

When applying the implant, a channel is first drilled in the head 41 of the femur in which channel the main screw 3 (according to the illustrated embodiment) is passed once threads have been formed by a threaded pin on the inner wall of the channel. This is often preceded (among other things in order to check the direction and alignment of the channel) by the drilling of a small hole, whereafter a guide wire is passed in and up through the head of the femur. In order to be able to use this technique, the screw 3 is normally provided with an axial through aperture. When the channel has been drilled and the entry hole broadened in the radial direction to receive the sleeve, and once the main screw 3 has been screwed into the head 41 of the femur, the sleeve 10 is passed in onto the screw shaft 32.

The next step for the orthopedist is to determine where the holder 2 is to be placed in order to provide maximum support but nevertheless make possible sufficient sliding along the sliding portion 21 of the holder. When this position has been determined, holes are drilled for the anchorage screws 5 in the shaft 40 of the femur, whereafter the anchorage screws 5 are screwed in place in order to fix the holder 2 in relation to the shaft 40 of the femur. Before the holder 2 is finally fixed at the shaft 40 of the femur, a locking screw 4 may, if this is considered necessary, be screwed into the bottom of the screw 3 inserted in the head of the femur.

Forces are normally exercised on the femur substantially in two directions, partly in the major direction of the head and neck of the femur (which are guided via the screw 3 and the sleeve 10 inserted in the head 41 of the femur), and partly along the shaft 40 of the femur. The forces in a direction of the head and neck of the femur are guided via the main screw 3 and the sleeve 10, and the forces along the shaft 40 of the femur are guided by the sliding portions 11 and 21 of the holder 2 and the angle element 1. The muscular contraction which takes place when the patient recovers from the anaesthetics exerts a relatively powerful compression in the direction of the shaft 40 of the femur.

Movements along the shaft 40 of the femur occur on healing as a rule amounting to several cm and normally lie in the range of between 0–2 cm. The movement transversely of the shaft of the femur is substantially less and lies normally in the range of between 0–8 mm.

The implant according to the invention unites the requirement of stability of the implant with the requirement on restrictive movement between the meeting surfaces of the fracture. Thus, employment of the implant affords the postoperative possibility of permitting a movement, between the fracture surfaces, predetermined by the orthopedist, in the longitudinal direction of the shaft of the femur and a mobility, determined by the dimensions of the implant, transversely of the longitudinal direction of the shaft of the femur. Since minor movements in a fracture promote the healing process, the above-disclosed movements in the longitudinal and lateral directions entail that a stimulation of the healing process is achieved. It should be particularly noted that the above-disclosed movements in the lateral direction afford the possibility of rectifying the fracture surfaces so that these mutually adapt and assume a well compressed position for the fracture, at the same time as the pumping effects occurring on movement between the fracture surfaces is utilized to the full for promoting the healing process.

In certain practical applications, it is desirable to restrict the maximum downward sliding of the angle element 1 in relation to the holder 2. The thickened portion 16 in the transitional region 14 of the angle element 1 restricts the upward movement of the holder 2 towards the main screw 3. When this stop function is to be employed, the orthopedist places the holder 2 in such a position that the distance between the upper edge 20 of the holder and the thickened portion 16 of the angle element 1 corresponds to the length of the maximum movement which can be permitted in the longitudinal direction of the shaft of the femur.

Given that the side of the holder 2 which is intended to be turned to face towards the shaft 40 of the femur including the flange portions 24 of the holder is of concave form, the anchorage screws 5 may, after application, be disposed crosswise in the shaft 40 of the femur. (FIG. 10).

In order, in an operation, that the holder 2 and the angle element 1 are not unintentionally separated from one another before the implant is applied, a stop device is provided in certain embodiments, which at least temporarily fixes the slide 11 of the angle element 1 in relation to the holder 2.

Figure 5A:
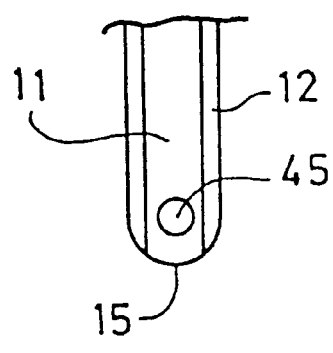
Figure 5B:
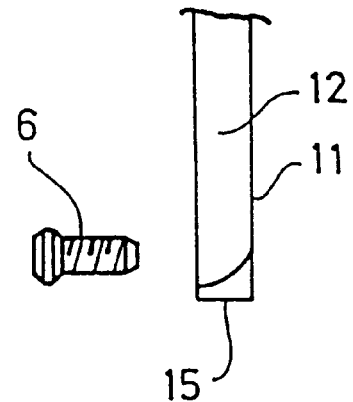

In embodiments according to FIG. 5, the fixing disclosed in the preceding paragraph is effected by means of a locking screw 6 which is accommodated in a threaded through aperture 45 in the slide 11. The temporary locking is effected in that the locking screw 6 is screwed into contact the bottom of the groove 21 of the holder 2, the slide being raised from the bottom and pressed against and locked by the sloping side walls 22 of the groove. In one alternative application, locking is effected in that the locking screw 6 is screwed in only so far that its tip projects out beneath the slide 11 when the aperture 45 is located beneath the lower edge 23 of the holder 2. The concept here is that the locking screw 6 is backed off once the implant has been in the femur.

In the embodiment according to FIG. 6a, locking of the angle element 1 takes place with the aid of friction, in that the side walls 12 and 22 of each respective sliding portion 11, 21 are provided with friction surfaces 19. Only the friction surface on the slide 11 is shown in FIG. 6a.

In alternative embodiments, the temporary locking is provided with the aid of rubber plugs, etc.

In a further alternative embodiment, locking is effected by means of a ball resiliently depressed into an opening in the bottom of the groove 21. The ball forces the side walls 12 of the slide 11 upwards towards the side walls 22 of the groove 21 with a force which is sufficient to prevent sliding movements between the sliding portions 11,21.

In yet a further alternative embodiment shown in FIG. 6b, the ball is replaced by a plate 50 tension by springs 51. The upwardly directed force on the slide 11 is, in the two above-disclosed embodiments, sufficiently great for the parts not to become separated by the action of, for example, force of gravity but is not so great that the parts are prevented from being displaced in relation to one another in the normal muscular and loading forces which prevail as described above.

In one alternative embodiment, the angle element 1 displays a groove which surrounds a ridge-like elevation 29 on the holder 2, the groove and the elevation 29 forming the sliding portions (FIG. 8).

If the holder 2 is placed too far down on the shaft 40 of the femur, there is a risk that the end 15 of the slide 11 will be so high in the groove 21 that the abutment between the side walls 12,22 is insufficient to withstand the torque forces which occur, in which event either the holder 2 or the slide 11 will break. In order to prevent this, a mechanical abutment is provided in certain embodiments, this preventing the end 15 of the slide 11 from coming too high in the groove 21. In the embodiment according to FIG. 7a, this abutment consists of a spring-pretensioned 26 pin 27 which cooperates with a locking aperture 17 in the slide 11. This locking arrangement may also function as a temporary stop for inadvertent sliding movements in accordance with the above.

Instead of a mechanical stop member, the slide 11 and the holder 2 have, in the embodiment shown in FIG. 7b, been provided with markings 18,28 which must not pass one another in order to avoid the risk of breakage of the implant as contemplated above. The markings consist of scribings, scorings, inlays of different colors, etc. In one alternative embodiment, only one of the sliding portions 11,22 is provided with a marking, while the end of the other sliding portion constitutes a second marking.

In the above description of the illustrated embodiment, we have taken as a point of departure the situation when the implant is employed for fixing intertrochanterian 42 and subtrochanterian 43 fractures. As was disclosed in the introduction of the specification, the implant according to the present invention can also be employed for supracondylar fractures, in which event the sleeve 10 will, however, be disposed further down, the angle a being then between 80° and 100°. Preferably, the angle α varies between 90° and 100°, and, as a rule is approx. 90°.

When use is made, in the body of this description, of expressions such as upper, lower, etc., these generally relate only to those directions in the FIGS. to which they refer.

Even though the description above has concentrated on femoral fractures, it will be obvious to a person skilled in the art that the implant according to the present invention is conceivable for use also in fractures to other bones, such as bones of the lower leg and the forearm.

What is claimed is:

1. An implant for fixing femoral fractures comprising a first part, a second part and an anchorage device; said first part including a sleeve for receiving said anchorage device, said sleeve being adapted for insertion in a channel provided in the head of a femur, said first part further including a slide, said sleeve being permanently fixed at an angle to said slide and including a throughgoing central cavity with an opening facing towards said slide, said slide being intended to be disposed in a longitudinal direction along the shaft of the femur and forming a sliding portion; said second part including a sliding portion which is axially and slidably engaged with said sliding portion of said first part, said second part having apertures located laterally outside said sliding portion of the second part for receiving anchorage screws intended to be secured in the shaft of the femur; said anchorage device being adapted for being secured in the head of the femur and disposed to be received by said sleeve, said first and second parts being respectively securable to the femur by said anchorage device and by said anchorage screws such that said sliding portions of said first and second parts are free to undergo relative axial and sliding movement in response to load applied to the femur, wherein said sliding portions are engaged with transverse clearance to permit movement relative to one another transversely of the longitudinal direction of the shaft of the femur by a restricted amount to provide maximum transverse displacement of said opening of said central cavity of about 7 mm from a neutral position in which the sliding portions of said first and second parts are longitudinally aligned and centered.

2. The implant as claimed in claim 1, wherein said sliding portion of said second part is formed by a groove open at both its ends; and the slide of said first part includes, in a transitional region to said sleeve, a cross-sectional alteration which, at a predetermined position, prevents continued relative sliding movement of said sliding portion of said second part in a direction towards said sleeve.

3. The implant as claimed in claim 1, wherein said second part comprises a holder provided with said sliding portion in the form of a groove which is upwardly open; said groove is extended along the entire axial extent of said holder; said groove of said holder having, in cross-section, sloping inner side walls which form the sliding surfaces of the second part, said groove having a width between said walls which decreases upwardly; said sliding portion of said first part having a cross-sectional configuration with sloping side walls which form the sliding surfaces of the first part slidably fitted in said groove in said holder with said transverse clearance to permit the relative movement of said sliding portions and said transverse displacement of said sliding portions.

4. The implant as claimed in claim 1, wherein a groove is provided in said slide of said first part, said groove receiving said sliding portion of said second part for said relative transverse displacement as well as relative longitudinal displacement.

5. The implant as claimed in claim 1, comprising an arrangement for temporarily fixing said sliding portion of said first part in relation to said sliding portion of said second part, and means for preventing said sliding portions of said first part and said second part from sliding apart.

6. The implant as claimed in claim 5, wherein said arrangement for temporarily fixing said sliding portions of said first and second parts comprises a locking screw, and an aperture for receiving said locking screw disposed adjacent to a lower end of said sliding portion of said first part, said aperture being oriented such that a tip of said locking screw locks against said sliding portion of said second part.

7. The implant as claimed in claim 5, wherein said arrangement for temporarily fixing said sliding portions of said first and second parts comprises friction surfaces disposed on sides of said sliding portions of said first and second parts facing one another.

8. The implant as claimed in claim 5, wherein said arrangement for temporarily fixing said sliding portions of said first and second parts comprises a spring-tensioned pin on said sliding portion of one part which bears against said sliding portion of the other part.

9. The implant as claimed in claim 5, wherein said means for preventing said sliding portions from sliding apart comprises a spring-tensioned pin on said sliding portion of one part which cooperates with an aperture in said sliding portion of the other part.

10. The implant as claimed in claim 5, wherein said means for preventing said sliding portions from sliding apart comprises marking means on each respective sliding portion of said first and said second parts to indicate positions beyond which said sliding portions are not to pass one another.

11. The implant as claimed in claim 1, wherein the axial extent of said second part is equal to or less than the axial extent of said sliding portion of said first part.

12. An implant for fixing femoral fractures comprising a first part, a second part and an anchorage device; said first part including a sleeve for insertion in a channel provided in the head of a femur, said first part further including a slide, said sleeve being permanently fixed at an angle to said slide, said slide being intended to be extended along a longitudinal direction of the shaft of the femur and forming a sliding portion; said second part including a sliding portion which has sliding surfaces axially and slidably engaged with sliding surfaces of the sliding portion of said first part, said second part having apertures located laterally offset from said sliding surfaces of said second part for receiving anchorage screws intended to be secured in the shaft of the femur; said anchorage device being adapted for being secured in the head of the femur and disposed to be received by said sleeve, said slide having a lower end which can freely pass a lower end of said sliding portion of said second part; said slide having, in a transitional region to said sleeve, a cross-sectional alteration which, at a predetermined position of said sliding portions prevents continued relative sliding movement of said sliding portion of said second part in a direction towards said sleeve, said first and second parts being respectively securable to the femur by said anchorage device and by said anchorage screws and being slidably connected to one another by said sliding surfaces of said first and second parts so that said sliding portions of said first and second parts are free to undergo relative axial sliding movement in response to load applied to the femur.

13. The implant as claimed in claim 12, wherein the sliding portion of said second part is formed by a groove open at both its ends.

14. The implant as claimed in claim 12, wherein said second part comprises a holder with said sliding portion thereof in the form of a groove which is upwardly open; said groove is extended along the entire axial extent of said holder; said groove in said holder having, in cross-section, sloping inner side walls which form said sliding surfaces of said second part, said groove having a width between said side walls which decreases upwardly; said sliding portion of said first part having a cross-sectional configuration with sloping side walls forming the sliding surfaces of said first part and which are slidably fitted in said groove in said holder.

15. The implant as claimed in claim 12, wherein a groove is provided in said slide of said first part, said groove slidably receiving said sliding portion of said second part.

16. The implant as claimed in claim 12, comprising an arrangement for temporarily fixing said sliding portion of said first part in relation to said sliding portion of said second part, and means for preventing said sliding portions of said first part and said second part from sliding apart.

17. The implant as claimed in claim 16, wherein said arrangement for temporarily fixing said sliding portions of said first and second parts comprises a locking screw, and an aperture for receiving said locking screw disposed adjacent to a lower end of said sliding portion of said first part, said aperture being oriented such that a tip of said locking screw locks against said sliding portion of said second part.

18. The implant as claimed in claim 16, wherein said arrangement for temporarily fixing said sliding portions of said first and second parts comprises friction surfaces disposed on sides of said sliding portions of said first and second parts facing one another.

19. The implant as claimed in claim 16, wherein said arrangement for temporarily fixing said sliding portions of said first and second parts comprises a spring-tensioned pin on said sliding portion of one part which bears against said sliding portion of the other part.

20. The implant as claimed in claim 16, wherein said means for preventing said sliding portions from sliding apart comprises a spring-tensioned pin on said sliding portion of one part which cooperates with an aperture in said sliding portion of the other part.

21. The implant as claimed in claim 16, wherein said means for preventing said sliding portions from sliding apart comprises marking means on each respective sliding portion of said first and said second parts to indicate positions beyond which said sliding portions are not to pass one another.

22. The implant as claimed in claim 12, wherein the axial extent of said second part is equal to or less than the axial extent of said sliding portion of said first part.

* * * * *